United States Patent
Skinner et al.

(10) Patent No.: US 8,227,235 B2
(45) Date of Patent: Jul. 24, 2012

(54) COMPOSITIONS AND METHODS FOR CONTROLLING DISEASES IN ANIMALS

(75) Inventors: James Skinner, Sevierville, TN (US); Doug Rupp, Newton, NJ (US)

(73) Assignee: Alpharma, LLC, Wilmington, DE (US)

( * ) Notice: Subject to any disclaimer, the term of this patent is extended or adjusted under 35 U.S.C. 154(b) by 35 days.

(21) Appl. No.: 12/586,359

(22) Filed: Sep. 21, 2009

(65) Prior Publication Data

US 2010/0143417 A1 Jun. 10, 2010

Related U.S. Application Data

(60) Provisional application No. 61/187,316, filed on Jun. 16, 2009, provisional application No. 61/156,902, filed on Mar. 3, 2009, provisional application No. 61/121,258, filed on Dec. 10, 2008.

(51) Int. Cl.
*C12N 1/20* (2006.01)

(52) U.S. Cl. ............. 435/252.4; 424/197.11; 424/203.1; 435/252.1; 435/243; 435/254.2; 435/254.21; 435/255.1; 435/255.2; 435/252.9; 435/252.31; 435/252.5

(58) Field of Classification Search .................. None
See application file for complete search history.

(56) References Cited

U.S. PATENT DOCUMENTS

| | | | |
|---|---|---|---|
| 4,649,143 A * | 3/1987 | Kantor et al. ................ | 514/279 |
| 6,214,337 B1 * | 4/2001 | Hayen et al. ................ | 424/93.51 |
| 2005/0271643 A1 * | 12/2005 | Sorokulova et al. ..... | 424/93.462 |

OTHER PUBLICATIONS

Huyhebaert (2005, article entitled Alternatives for Antibiotics in Poultry, in Proceedings of the 3rd Mid-Atlantic Nutrition Conference, Zimmerman ed. Publidshed by the Maryland Feed Industry Council, pp. 38-57.*
Grilli et al., Pediocin A improves growth performance of broilers challenged with Clostridium perfringens, Poultry Sci. (2009), 2152-2158 vol. 88.
Gao et al., Effect of *Saccharomyces cerevisiae* fermentation product on immune functions of broiler challenged with Eimeria tenella Poultry Sci (2009) 2141-2151 vol. 88.
McReynolds et al., Efficacy of multistrain direct-fed microbial and phytogenetic products in reducing necrotic enteritis in commercial . . . Poultry Sci (2009) 2075-2080 vol. 88.
Martel et al., Susceptibility of Clostridium perfringens strains from broiler chickens to antibiotics and anticoccidials, Avian Path. (2004) 3-7, vol. 33(1).
Elwinger et al., The Effects of Narasin on Clotridium perfringens in Caeca and Occurence . . . , Proceedings XIX World's Poulty Congress (1992) 580-584 vol. 3.
Brennan et al., Efficacy of Narasin in the Prevention of Necrotic Enteritis in Broiler Chickens, Avian Diseases (2001) 210-214, vol. 45.

* cited by examiner

*Primary Examiner* — Jennifer Graser
(74) *Attorney, Agent, or Firm* — Martha A. Gammill

(57) ABSTRACT

Disclosed herein are compositions for the treatment of a disease in an animal including yeast extract of *Saccharomyces cerevisiae*, *Bacillus licheniformis* or *Bacillus subtilis* spores, and a carrier. Also included are animal feed compositions including the composition for the prevention, control and/or treatment of a disease in an animal and an animal's food/feed. The compositions are useful to prevent, control, and treat diseases such as necrotic enteritis in poultry when used in combination with an anticoccidal ionophore or coccidiosis vaccine.

7 Claims, No Drawings

COMPOSITIONS AND METHODS FOR CONTROLLING DISEASES IN ANIMALS

CROSS-REFERENCE TO RELATED APPLICATIONS

This application claims benefit under 35 USC §119(e) of U.S. Provisional patent Application Ser. No. 61/187,316 filed Jun. 16, 200, U.S. Provisional patent Application Ser. No. 61/156,902 filed Mar. 3, 2009 and U.S. Provisional patent Application Ser. No. 61/121,258 tiled Dec. 10, 2008.

BACKGROUND

Pigs and poultry, especially those which are intensively reared or reared in large-scale operations, have a tendency to suffer from or risk catching a variety of diseases and infections, for example, *Mycoplasma* diseases in pigs and poultry, Lawsonia infections (ileitis) and swine dysentery in pigs and necrotic enteritis in poultry. Medicaments have been proposed or used for the treatment of individual diseases or infections of these types.

*L. intracellularis*, the causative agent of porcine proliferative enteropathy (PPE; also called ileitis in swine), affects virtually all animals, including: rabbits, ferrets, hamsters, fox, horses, and other animals as diverse as ostriches and emus. PPE is a common diarrhea disease of growing-finishing and young breeding pigs characterized by hyperplasia and inflammation of the ileum and colon. It often is mild and self-limiting but sometimes causes persistent diarrhea, severe necrotic enteritis, or hemorrhagic enteritis with high mortality.

Necrotic enteritis (NE) in poultry is caused by a gram-positive, anaerobic bacteria *Clostridium perfringens*. The disease is an acute enterotoxemia condition primarily affecting 2-5 week old broiler chickens and 7-12 week old turkeys. The duration of the illness is very short, and typically the only sign of the disease is a sudden increase in mortality of the birds.

*C. perfringens* is a nearly ubiquitous bacteria found in soil, dust, feces, feed, and used poultry litter, and is also an inhabitant of the intestines of healthy chickens. The enterotoxemia that causes the necrotic enteritis occurs either following an alteration in the intestinal microflora or from a condition that results in damage to the intestinal mucosa (e.g., coccidiosis, mycotoxicosis, salmonellosis, ascarid larvae). High dietary levels of animal byproducts, wheat, barley, oats, or rye predispose birds to the disease. Anything that promotes excessive bacterial growth and toxin production or slows feed passage rate in the small intestine could promote the occurrence of necrotic enteritis.

Diagnosis of necrotic enteritis is based on gross lesions and a gram-stained smear of a mucosal scraping that exhibits large, gram-positive rods. The gross lesions are primarily found in the small intestine, which may be ballooned, friable, and contain a foul-smelling, brown fluid. The mucosa is usually covered with a tan to yellow pseudomembrane often referred to as a "Turkish towel" appearance. This pseudomembrane may extend throughout the small intestine or be only in a localized area. The disease persists in a flock for 5-10 days, and mortality is 2-50%. Conventional products for preventing necrotic enteritis in poultry are medicated feeds containing virginiamycin (20 g/ton feed), bacitracin (50 g/ton), and lincomycin (2 g/ton). Medicated feeds containing anticoccidial compounds in the ionophore class have also been helpful in preventing necrotic enteritis. Treatment for necrotic enteritis is typically by administering bacitracin, penicillin, and lincomycin in the drinking water for 5-7 days.

NE has been identified as a disease condition that may be prevented or controlled by use of Direct-Fed Microbials (DFM) products because they act on the intestinal microflora. Coccidiosis causes considerable economic loss in the poultry industry. The disease is caused by several species of *Eimeria* including *E. tenella, E. necatrix, E. acervulina, E. brunetti,* and *E. maxima*. Stages of coccidiosis in chicken appear both within the host as well as outside. The developmental stages in the chicken give rise to a microscopic egg (called an oocyst) that is passed out in the droppings. Normally, most birds pass small numbers of oocysts in their droppings without ill effects, but intensive rearing of domestic chickens provides conditions which permit the build-up of infective oocysts in the environment thereby increasing the possibility of coccidiosis infections. Coccidiosis infections can become noticeable by the third day of infection. Symptoms include chickens drooping, stopping feeding and huddling together. Blood starts to appear in the droppings by day four and by day eight the chickens are either dead or have started to recover.

Prevention of coccidiosis includes mixing anticoccidial drugs with feed. Ionophores such as salinomycin are the most commonly-used drugs in the US for coccidiosis prevention. Salinomycin and salts thereof are typically added to animal feed at a concentration of about 40 to about 60 grams per ton of animal feed (0.0044% to 0.0066%). Salimomycin sodium is the preferred form of salinomycin used in the United States. Narasin is the most commonly-reported ionophore promoted as an aid in NE prevention. Coccidiosis vaccines (Coccivac®-B) can also be used particularly by those wishing to market antibiotic-free chickens. Coccivac-B is a non-attenuated, live sporulated oocyst coccidiosis vaccine containing *E. acervulina, E. mivati, E. maxima* and *E. tenella.*

A need exists for compositions and methods to treat multiple diseases in animals, particularly diseases of bacterial origin. These compositions should be able to be used in combination with other treatments and/or compositions used for treating other diseases. Optimally the compositions for treatment of diseases would have a synergistic effect when combined either with other compositions or other treatment regimens.

BRIEF SUMMARY

The present invention is related to compositions and methods for treatment of disease in animals, particularly poultry. One embodiment of the invention is directed to a composition for the treatment of a disease in an animal that includes a yeast extract from *Saccharomyces cerevisiae, Bacillus licheniformis* spores, and optionally a carrier. An embodiment of the invention is also directed a method for preventing a disease in an animal that includes administering to an animal a composition containing yeast extract from *Saccharomyces cerevisiae, Bacillus licheniformis* spores, and optionally a carrier.

The present invention is also directed to a composition for the prevention and/or control of a disease in an animal which includes a yeast extract from *Saccharomyces cerevisiae* and QST-713 strain of *Bacillus subtilis*, and optionally a carrier. An embodiment of the invention is also directed to a method for preventing and/or controlling a disease in an animal that includes administering to the animal an effective amount of a composition containing a yeast extract from *Saccharomyces cerevisiae* and QST-713 strain of *Bacillus subtilis*, and optionally a carrier.

The present invention is further related to a composition containing about 50 wt % to about 90 wt % of the cell wall fraction from *Saccharomyces cerevisiae*; about 5 wt. % to about 50 wt. % of *Bacillus licheniformis* spores, comprising about $4.5\times10^9$ to about $2.5\times10^{10}$ spores per gram; and an anticoccidal ionophore. An embodiment of the invention is also directed to a method for preventing disease in an animal that includes vaccinating the animal with a coccidiosis vaccine and administering to the animal a composition containing about 50 wt. % to about 90 wt. % of the cell wall fraction from *Saccharomyces cerevisiae*; about 5 wt. % to about 50 wt. % of the *Bacillus licheniformis* spores, comprising about $4.5\times10^9$ to about $2.5\times10^{10}$ spores per gram; and about 0 wt. % to 45 wt. % of a carrier. An embodiment of the invention is additionally related to a method for decreasing the mortality in an animal challenged with *C. perfringens* that includes vaccinating the animal with a coccidiosis vaccine and administering to the animal a composition containing about 50 wt. % to about 90 wt. % of the cell wall fraction from *Saccharomyces cerevisiae*; about 5 wt. % to about 50 wt. % of the *Bacillus licheniformis* spores, comprising about $4.5\times10^9$ to about $2.5\times10^{10}$ spores per gram; and about 0 wt. % to 45 wt. % of a carrier. An embodiment of the invention is further directed to a method for decreasing the necrotic enteritis lesions in an animal challenged with *C. perfringens* which includes vaccinating the animal with a coccidiosis vaccine and administering to the animal a composition comprising about 50 wt. % to about 90 wt. % of the cell wall fraction from *Saccharomyces cerevisiae*; about 5 wt. % to about 50 wt. % of the *Bacillus licheniformis* spores, comprising about $4.5\times10^9$ to about $2.5\times10^{10}$ spores per gram; and about 0 wt. % to 45 wt. % of a carrier.

DETAILED DESCRIPTION

Disclosed herein are unexpectedly synergistic combinations of probiotic bacteria such as *B. licheniformis* and immune-enhancing yeast cell wall extracts comprising beta-glucans and mannans used for the prevention, control, and treatment of necrotic enteritis in combination with a coccidiostat or coccidiosis vaccine. These compositions (otherwise called an animal feed additive) suitable to treat diseases in an animal are particularly useful to treat diseases caused by infection with a bacterium such as *L. intracellularis* or *C. perfringens*.

Direct-Fed Microbials (DFM) are living microorganisms that are fed to animals to improve production by modulating the intestinal environment in the animal and by improving digestion. They help maintain the proper balance of normal gut flora in the gastrointestinal tract. Although scientists do not fully understand the mechanism of action of DFMs, it is believed that DFMs may act by attaching themselves to gut surfaces, reducing or preventing harmful organisms from attaching to and colonizing the gut surface; stimulating intestinal immunity that in turn provides protection against disease; releasing enzymes that aid in digestion; producing organic acids that alter the pH of the gut and stimulate beneficial organisms; and producing nutrients, such as vitamins. AlCare™ (Alpharma Inc. of Bridgewater, N.J.) is a DFM containing a modified strain of *B. licheniformis* (NCTC 13123). AlCare™ contains $1\times10^{10}$ spores of *B. licheniformis* per gram in 70 wt % of a calcium carbonate carrier. One pound of AJCare™ per ton of feed provides $2.2\times10^9$ colony forming units (cfu) *B. licheniformis* per pound of feed.

Brewer's yeast is a type of fungus known as *S. cerevisiae*. Alphamune® (Alpharma Inc. of Bridgewater, N.J.) is a cross-linked natural polysaccharide fiber produced from the cell walls of food grade brewer's yeast. The ingredients in Alphamune® are also made under the name of Beta Mos® (Alpharma Inc. of Bridgewater, N.J.), which is the cell wall fraction of *S. cerevisiae* after solubilizing and extracting the biological active materials from within the cell after autolysis. Alphamune® is a combination of beta-glucans and mannans. The beta-glucans present in Alphamune® have side chains (1,3-1,6) resulting in a specific complex structure which cannot be broken by glucanase. Beta-glucans have a strong immune enhancing effect in animals, binding to macrophages which are activated and secrete cytokines. The *S. cerevisiae* mannans are polysaccharide-polypeptide complexes which contain partially phosphorylated D-mannose residues. Mannans have been shown to have immunostimulatory effects. Alphamune® generally contains greater than or equal to about 24 wt. % of beta glucans and less than or equal to about 15 wt. % mannans.

Surprisingly, a combination, and compositions thereof, of QST-713 strain of *Bacillus subtilis*, sold as a biofungicide, and a yeast extract such as that from *Saccharomyces cerevisiae* containing beta-glucans and mannans, i.e., brewer's yeast, may be employed to prevent and/or control diseases, such as infections in animals caused by a bacterium, e.g., *L. intracellularis* or *Clostridium perfringens*.

As described herein above, the present invention further provides a composition comprising QST-713 strain of *Bacillus subtilis* and a yeast extract such as that from *Saccharomyces cerevisiae*, and optionally a carrier, for the prevention and/or control of diseases in animals, such as infections, in particular, necrotic enteritis in poultry and swine ileitis in pigs.

QST-713 strain of *Bacillus subtilis* is commercially available as a biofungicide under the trade name Serenade® MAX (AgraQuest Inc. of Davis, Calif.). Serenade® MAX is a microbial pesticide based on a naturally occurring strain QST-713 of *Bacillus subtilis*. It produces three groups of lipopeptides: iturins, agrastatins/plipastatins and surfactins that act synergistically to inhibit germ tubes, mycelium and bacterial cells. Serenade® MAX contains 10-15 wt-% of dried *Bacillus subtilis* QST-715 in a carrier comprising a mixture of inert, non-reactive ingredients and provides a minimum of $7.3\times10^9$ cfu of *Bacillus subtilis* QST-715 per gram of the mixture. Serenade® MAX can be formulated as a wettable powder, a wettable granule and an aqueous suspension that are applied like any other foliar fungicide. Serenade® MAX is not toxic to non-target and beneficial organisms. Due to Serenade's complex mode of action, environmental friendliness, and broad spectrum control, it is well suited for use in Integrated Pest Management.

As indicated herein above, the composition of the present invention comprises QST-713 strain of *Bacillus subtilis* and a yeast extract such as that from *Saccharomyces cerevisiae*, and optionally a carrier. Preferably, the composition of the present invention comprises the QST-713 strain of *Bacillus subtilis* in an amount ranging from about 5 wt % to about 50 wt %, and more preferably, from about 10 wt % to about 15 wt %, based on the total weight of the composition. Preferably, the QST-713 strain of *Bacillus subtilis* component of the composition of the present invention contains from about $4.5\times10^9$ to about $2.5\times10^{10}$ cfu of QST-713 strain of *Bacillus subtilis* per gram and, more preferably, a minimum of about $7.3\times10^9$ cfu of QST-713 strain of *Bacillus subtilis* per gram. As described herein above, the present invention further provides an animal feed composition comprising a combination of QST-713 strain of *Bacillus subtilis* and a yeast extract such as that from *Saccharomyces cerevisiae* for the prevention and/or control of diseases such as infections in animals, in particular, necrotic enteritis in poultry and swine ileitis in pigs.

One embodiment of the invention includes a composition for the prevention of disease in an animal comprising a yeast extract from yeast such as *S. cerevisiae*, a probiotic bacterium and an anticoccidal ionophore. Anticoccidal ionophores include, but are not limited to salinomycin, monensin, nigericin, narasin, laidlomycin, noboritomycin, grisorixin, mutalomycin, alborixin, lonomycin, lasalocid maduramicin ammonium, semduramicin, and lysecellin. A preferred embodiment of the invention includes salinomycin (Bio-Cox®; Alpharma Inc. of Bridgewater, N.J.). The anticoccidal ionophone is present in an amount ranging from about 0.0033 wt. % to about 0.0099 wt. %, preferably from about 0.0044 wt. % to about 0.0066 wt. %.

An embodiment of the invention is directed to a method for preventing disease in an animal which includes vaccinating the animal with a coccidiosis vaccine and administering to the animal a composition that contains yeast such as *S. Cerevisiae*, a probiotic bacterium, and a carrier. A preferred coccidiosis vaccine is Coccivac®-B (Schering Plough Animal Health Corporation), a non-attenuated, live sporulated oocyst coccidiosis vaccine containing *E. acervuline, E. mivati, E. maxima* and *E. tenella*.

The composition optionally comprises a carrier. A number of suitable dry carriers may be organic or inorganic. Exemplary inorganic carriers include, salts such as calcium carbonate, calcium sulfate, and the like. Suitable organic carriers include lactose and the like. Small amounts of other flow control agents, for example silica, may also be used. Mixtures comprising one or more of the foregoing may also be used.

The composition comprises a yeast extract such as one from *S. cerevisiae*. Specifically, the cell wall fraction comprises beta-glucans and mannans. The cell wall fraction is produced, for example, by mechanically ruptured cells. The yeast extract is present in an amount of about 50 wt. % to about 90 wt. %, specifically about 50 wt. % to about 85 wt. % and more specifically about 50 wt. % to about 55 wt. %, based on the total weight of the composition. In one embodiment, the beta-glucan has (1,3-1,6) side chains and is resistant to cleavage by glucanase. In another embodiment, the mannans are polysaccharide-polypeptide complexes, partially phosphorylated D-mannose residues. The yeast extract comprises about 40 wt. % to about 85 wt. % cell walls, specifically about 40 wt. % to about 45 wt. % cell walls.

*B. licheniformis* is present in an amount of about 5 wt. % to about 50 wt. %, and specifically about 7.5 wt. % to about 12.5 wt. %, based on the total weight of the composition. The *B. licheniformis* component comprises about $4.5 \times 10^9$ to about $2.5 \times 10^{10}$ cfu per gram, and specifically about $5 \times 10^9$ to about $1.25 \times 10^{10}$ cfu per gram, based on the total weight of the composition.

The carrier is present in an amount of 0 wt. % to 45 wt. %, specifically about 5 wt. % to about 40 wt. %, and more specifically about 37.5 wt. % to about 42.5 wt. %, based on the total weight of the composition.

In one embodiment, the composition suitable for treatment of a disease in an animal is administered in an animal foodstuff. Manufactured foodstuffs for animals such as cattle, pigs, and fowl are usually provided in the form of pellets or similar particulate material. Pellets are typically manufactured by combining a cereal base with ingredients such as oil and protein, steam conditioning the mixture (for example at 70° C. for 5 minutes), extruding the mixture through a circular die (typically between 2 mm and 15 mm in diameter), cutting into appropriately sized lengths (e.g., 5-20 mm), and drying. The finished pellets are generally cylindrically shaped and have a relatively smooth surface.

In one embodiment, an animal feed composition is prepared by adding an animal feed additive composition to an animal foodstuff. The animal feed additive composition may be added to the food in a number of ways. The animal feed additive composition containing a given quantity of active ingredients may be added to a given quantity of feed and mixed or blended to provide a substantially homogeneous medicated feed composition. Large feed lots may be prepared in this manner for treating a large number of animals. Alternatively, feed batches containing feed for a single animal or single meal may be prepared either by mixing a predetermined quantity of animal feed additive composition with the animal feed or by adding a predetermined quantity of premix to an animal's feed as a top dressing.

In another embodiment, an animal feed composition comprises a composition suitable for treatment of a disease in an animal and an animal foodstuff, wherein the composition suitable for treatment of a disease in an animal is present in an amount of about 0.5 pounds to about 10 pounds, specifically about 1 pound to about 5 pounds, more specifically about 1.5 pounds to about 2.5 pounds, and most specifically 2 pounds of the composition suitable for treatment of a disease in an animal to a ton of animal foodstuff (mash or pellet forms). In one embodiment, the animal foodstuff may be a poultry foodstuff. In another embodiment, the animal foodstuff may be a swine foodstuff.

The invention is further illustrated by the following non-limiting examples.

EXAMPLES

Example 1

One-day-old healthy broiler male chicks (Cobb×Cobb) chicks were obtained from Cobb-Vantress Hatchery of Cleveland, Ga. Upon arrival, the chicks were raised in Petersime battery cages. Eight birds were placed in each cage. A thermostatically controlled gas furnace/air conditioner maintained uniform temperature and even continuous illumination was provided. Water was available ad libitum through the trial. The chicks were divided into groups containing 48 chicks. Two control treatment groups were fed an unmedicated commercial type chicken starter ration compounded with feedstuffs commonly used in the United States. One group (designated AlCare 0.5 Group) was fed AlCare™ (Alpharma of Bridgewater, N.J.), a DFM product containing $1.0 \times 10^{10}$ spores of *B. Licheniformis* per gram, at a rate of 0.5 pound per ton. Another group (AlCare 1 Group) was fed AlCare™ at a rate of 1.0 pound per ton. Two separate groups were fed Alphamune® (Alpharma of Bridgewater, N.J.), a brewer's yeast (*Saccharomyces cerevisiae*) extract for use in animal feeds, at a rate of 1 pound per ton (Alphamune 1 Group) and 2 pounds per ton (Alphamune 2 Group), respectively. Further groups were fed both AlCare and Alphamune at rates of AlCare 0.5 pound per ton plus Alphamune 1 pound per ton, AlCare 1 pound per ton plus Alphamune 1 pound per ton, AlCare 0.5 pound per ton plus Alphamune 2 pounds per ton, and AlCare 1 pound per ton plus Alphamune 2 pounds per ton.

The chicks were fed for 28 days. All dead birds dying during the study were weighed and necropsied for the presence of necrotic enteritis (NE) lesions. All groups were challenged orally with *Eimeria maxima* (5,000 oocysts per bird) on Day 14. All treatments except a control (NC) were challenged with *C. perfringens* (broth culture of *C. perfringens* $10^8$ cfu/ml) on days 19, 20, and 21. On Day 22, three birds from each cage were lesion scored for NE. The trail was terminated on day 28. The results of the trials are shown in Table 1.

TABLE 1

| Treatments | Necrotic Enteritis Lesion Score | Mortality % Necrotic Enteritis |
|---|---|---|
| Control | 0 | 0 |
| Challenged Control | 1.11 | 20.83 |
| AlCare 0.5 | 0.56 | 6.25 |
| AlCare 1 | 0.56 | 6.25 |
| Alphamune 1 | 0.72 | 10.42 |
| Alphamune 2 | 0.94 | 12.50 |
| AlCare 0.5 + Alphamune 1 | 0.44 | 12.50 |
| AlCare 1 + Alphamune 1 | 0.28 | 2.08 |
| AlCare 0.5 + Alphamune 2 | 0.72 | 10.42 |
| AlCare 1 + Alphamune 2 | 0.56 | 6.25 |

Example 2

One-day-old healthy broiler male chicks (Cobb×Cobb) chicks were obtained from Cobb-Vantress Hatchery of Cleveland, Ga. Upon arrival, fifty birds were allocated to each treatment pen by blocks. For environmental control there were ambient humidity and twenty-four hour lighting. Gas heaters were the primary heat source with a heat lamp in each pen for supplemental heat as required during the brooding period. Fans and sidewall curtains manipulation were used for ventilation and to cool the birds. Water was available ad libitum through the trial. Two control treatment groups were fed a non-medicated commercial type chicken starter, grower and finisher rations compounded with foodstuffs commonly used in the United States. One group, designated as SM Group, was fed Serenade® MAX at a rate of 91 g per ton of foodstuff. Another group, designated as SM+Alphamune® (AM) Group, was fed both Serenade® MAX at a rate of 91 g per ton of foodstuff and Alphamune® at a rate of 1 lb per ton of foodstuff. The treatments were replicated in six blocks and randomized.

The chicks were fed ad libitum from the date of chick arrival until Day 42 of the study. All dead birds dying during the study were weighed and necropsied for the presence of necrotic enteritis (NE) lesions. All groups were challenged orally with Eimeria maxima (5,000 oocysts per bird) on Day 14. All treatment groups except one of the control groups (NC) were challenged with C. perfringens (CP, broth culture of C. perfringens $10^8$ cfu/mL) on days 19, 20 and 21. On Day 22, five birds from each pen were lesion scored for NE. The trial was terminated on day 42, and the results are shown in Table 2.

TABLE 2

| Treatments | Necrotic Enteritis Lesion Score | Mortality % Necrotic Enteritis |
|---|---|---|
| Control (NC) | 0.17 | 1.00 |
| Challenged Control (CP) | 1.30 | 30.33 |
| Serenade ® MAX (SM); CP | 0.77 | 21.00 |
| SM + Alphamune ® (AM); CP | 0.50 | 17.00 |

Example 3

One-day-old healthy male broiler chicks (Cobb×Cobb) were obtained from a hatchery where they were sexed and received routine vaccination (HVTSB1). Only healthy-appearing chicks were used in the study. No birds were replaced during the course of the study. Upon arrival, chicks were raised in litter floor pens. There were 50 birds placed per pen. Pens were blocked by location in the house. Each treatment appeared once within each block. Thermostatically-controlled gas furnaces maintained uniform temperature. Water was available ad libitum throughout the trial.

All birds were weighed by pen on days 0, 21, and 42. Starter, grower, and finisher feed consumptions were measured from days 0 to 21, 21 to 35, and 35 to 42, respectively. The study was terminated on day 42. On Day 22, five birds from each pen were lesion scored for NE. The scoring was based on a 0 to 3 score, with 0 being normal and 3 being the most severe. The scoring was as follows: 0 for normal intestines, 1 for slight mucus covering and loss of tone, 2 for severe necrotizing enteritis, and 3 for extreme necrotizing enteritis with presence of blood in the lumen. Birds dying during the study were weighed and necropsied for the presence of NE. All birds from the study were disposed of at the research facility. Mortality was summarized as total and those resulting from NE.

A total of eight different regimens were tested. All groups were challenged orally with Eimeria maxima (5,000 oocysts per bird) on Day 14. All treatments except a control (NC) and a treatment group with AlCare and Alphamune (Group AA-NC) were challenged with C. perfringens (broth culture of C. perfringens $10^8$ cfu/ml) on days 19, 20, and 21. Control feeds did not contain AlCare™ (AC), Alphamune® (AM), or Salinomycin (S). Control groups were not spray vaccinated using a Spraycox® (Schering Plough Animal Health Corporation) machine with the label recommended dosage on day of hatch. The groups were designated as follows:

Group NC (unchallenged control): Group NC was fed an unmedicated commercial type chicken starter ration compounded with feedstuffs commonly used in the United States and was unchallenged by C. perfringens.

Group CP (challenged control): Group CP was fed an unmedicated commercial type chicken starter ration compounded with feedstuffs commonly used in the United States and was challenged by C. perfringens as described above.

Group AA, NC (AlCare™ and Alphamune® fed; unchallenged): Group AA, NC was fed a commercial type chicken starter ration compounded with feedstuffs commonly used in the United States plus AlCare™ at a rate of 1.0 pound per ton and Alphamune® at a rate of 1 pound per ton. This group was not challenged.

Group AA, CP (AlCare™ and Alphamune® fed; challenged) was fed a commercial type chicken starter ration compounded with feedstuffs commonly used in the United States plus AlCare™ at a rate of 1.0 pound per ton and Alphamune® at a rate of 1 pound per ton. This group was challenged as described above.

Group S, CP (salinomycin treated, challenged) was fed a commercial type chicken starter ration compounded with feedstuffs commonly used in the United States plus salinomycin (66 ppm) and was challenged as described above.

Group S, AA, CP (salinomycin treated, AlCare™ and Alphamune® fed; challenged) was fed a commercial type chicken starter ration compounded with feedstuffs commonly used in the United States plus AlCare™ at a rate of 1.0 pound per ton and Alphamune® at a rate of 1 pound per ton plus salinomycin (66 ppm). This group was challenged as described above.

Group CV, CP (Coccivac®-B treated; challenged) was spray vaccinated using a Spraycox® machine (Schering-Plough Animal Health Corporation) with the label recommended dosage on day of hatch and fed was fed a commercial type chicken starter ration compounded with feedstuffs commonly used in the United States. This group was challenged as described above.

Group CV, AA, CP (Coccivac®-B treated; challenged) was spray vaccinated using a Spraycox® machine with the label recommended dosage on day of hatch and fed was fed a commercial type chicken starter ration compounded with feedstuffs commonly used in the United States plus AlCare™ at a rate of 1.0 pound per ton and Alphamune® at a rate of 1 pound per ton. This group was challenged as described above.

Statistics were carried out using SAS® (SAS Institute, Inc., Cary, N.C., USA, 2002) in the analyses of the data. Additional analyses were performed comparing AA with the anticoccidial program with and without AA.

Calculations of pen data used in the statistical analyses were performed using SAS. Average bird weight gains were calculated for the 0 to 21, 0 to 42, and 21 to 42-days periods. For the NE lesion scores, the pen average of the five birds selected for NE lesion scoring on Day 22 were calculated. The feed conversion ratio (FCR) was calculated on a pen basis for the 0 to 21, 0 to 42, and 21 to 42 days periods with adjustments made for dead and removed birds. The percentages of total mortality and those mortalities caused by NE were calculated. Any reference made to the performance of the chickens would be referring to effects on weight gain and/or FCR.

This study was conducted using a randomized complete block design.

There were 6 blocks. The pen of birds was the experimental unit. The model included block and treatment. Block was a random effect. Treatment was a fixed effect, so the model was mixed.

The summary variables include performance data and data related to the NE challenge for each pen. A mixed model analysis was performed on the data using the PROC MIXED procedure of SAS.

The results of the trials are shown in Tables 3-8. In the tables the following abbreviations are used:

AA=AlCare+Alphamune

S=salinomycin

CV=Coccivac®-B

CP=Challenged

NC=Not Challenged

TABLE 3

Effects of dietary AlCare plus Alphamune on weight gains of broiler chickens in a *Clostridium perfringens* challenge model in litter floor pens.

| Treatments | Average weight (kg) Day 0 | Average Weight Gain (kg) | | |
| --- | --- | --- | --- | --- |
| | | Days 0 to 21 | Days 0 to 42 | Days 21 to 42 |
| Control (NC) | .044 | .515 | 1.892 | 1.377 |
| Challenge Control (CP) | .044 | .469 | 1.704 | 1.235 |
| AA, NC | .044 | .497 | 1.899 | 1.403 |
| AA, CP | .044 | .488 | 1.861 | 1.373 |
| S, CP | .044 | .511 | 1.993 | 1.482 |
| S, AA, CP | .044 | .556 | 2.085 | 1.529 |
| CV, CP | .044 | .479 | 1.923 | 1.443 |
| CV, AA, CP | .044 | .501 | 2.017 | 1.516 |

TABLE 4

Effects of dietary AlCare plus Alphamune on feed conversion and necrotic enteritis lesions of broiler chickens in a *Clostridium perfringens* challenge model in litter floor pens.

| Treatments | Feed Conversion Ratio (feed to gain ratio) | | | Necrotic Enteritis Lesion Score |
| --- | --- | --- | --- | --- |
| | Days 0 to 21 | Days 0 to 42 | Days 21 to 42 | |
| Control (NC) | 1.723 | 1.943 | 2.055 | 0.17 |
| Challenged Control (CP) | 1.893 | 2.051 | 2.183 | 1.30 |
| AA, NC | 1.759 | 1.896 | 1.962 | 0.20 |
| AA, CP | 1.763 | 1.921 | 2.016 | 0.60 |
| S, CP | 1.688 | 1.876 | 1.963 | 0.07 |
| S, AA, CP | 1.647 | 1.824 | 1.910 | 0.17 |
| CV, CP | 1.792 | 1.893 | 1.950 | 0.30 |
| CV, AA, CP | 1.737 | 1.823 | 1.867 | 0.33 |

TABLE 5

Effects of dietary AlCare plus Alphamune on mortality of broiler chickens in a *Clostridium perfringens* challenge model in litter floor pens.

| Treatments | Mortality (%) | | |
| --- | --- | --- | --- |
| | All Causes | | Necrotic Enteritis |
| | Days 0 to 21 | Days 0 to 42 | Days 0 to 42 |
| Control (NC) | 3.00 | 9.00 | 1.00 |
| Challenged Control (CP) | 5.33 | 35.67 | 30.33 |
| AA, NC | 4.00 | 9.33 | 2.67 |
| AA, CP | 2.33 | 18.67 | 11.67 |
| S, CP | 3.33 | 6.00 | 1.6 |
| S, AA, CP | 4.33 | 7.67 | 1.00 |
| CV, CP | 4.33 | 25.00 | 19.67 |
| CV, AA, CP | 4.00 | 13.67 | 5.67 |

TABLE 6

Effects of dietary AlCare plus Alphamune on weight gains of broiler chickens in a *Clostridium perfringens* challenge model in litter floor pens.

| Treatments | Average weight (kg) Day 0 | Average Weight Gain (kg) | | |
| --- | --- | --- | --- | --- |
| | | Days 0 to 21 | Days 0 to 42 | Days 21 to 42 |
| Control (NC) | .044 | .515 | 1.892 | 1.377 |
| Challenged Control (CP) | .044 | .469 | 1.704 | 1.235 |
| S, CP | .044 | .511 | 1.993 | 1.482 |
| S, AA, CP | .044 | .556 | 2.085 | 1.529 |
| CV, CP | .044 | .479 | 1.923 | 1.443 |
| CV, AA, CP | .044 | .501 | 2.017 | 1.516 |

TABLE 7

Effects of dietary AlCare plus Alphamune on feed conversion and necrotic enteritis lesions of broiler chickens in a *Clostridium perfringens* challenge model in litter floor pens.

| Treatments | Feed Conversion Ratio (feed to gain ratio) | | | Necrotic Enteritis Lesion Score |
| --- | --- | --- | --- | --- |
| | Days 0 to 21 | Days 0 to 42 | Days 21 to 42 | |
| Control (NC) | 1.723 | 1.943 | 2.055 | 0.17 |
| Challenged Control (CP) | 1.893 | 2.051 | 2.183 | 1.30 |
| S, CP | 1.688 | 1.876 | 1.963 | 0.07 |
| S, AA, CP | 1.647 | 1.824 | 1.910 | 0.17 |

TABLE 7-continued

Effects of dietary AlCare plus Alphamune on feed conversion and necrotic enteritis lesions of broiler chickens in a *Clostridium perfringens* challenge model in litter floor pens.

| Treatments | Feed Conversion Ratio (feed to gain ratio) | | | Necrotic Enteritis Lesion Score |
|---|---|---|---|---|
| | Days 0 to 21 | Days 0 to 42 | Days 21 to 42 | |
| CV, CP | 1.792 | 1.893 | 1.950 | 0.30 |
| CV, AA, CP | 1.737 | 1.823 | 1.867 | 0.33 |

TABLE 8

Effects of dietary AlCare plus Alphamune on mortality of broiler chickens in a *Clostridium perfringens* challenge model in litter floor pens.

| Treatments | Mortality (%) | | |
|---|---|---|---|
| | All Causes | | Necrotic Enteritis |
| | Days 0 to 21 | Days 0 to 42 | Days 0 to 42 |
| Control (NC) | 3.00 | 9.00 | 1.00 |
| Challenged Control (CP) | 5.33 | 35.67 | 30.33 |
| S, CP | 3.33 | 6.00 | 1.67 |
| S, AA, CP | 4.33 | 7.67 | 1.00 |
| CV, CP | 4.33 | 25.00 | 19.67 |
| CV, AA, CP | 4.00 | 13.67 | 5.67 |

Data in Tables 3, 4, and 5 are the comparisons of between the AACP treatments and the S and CV treatments with and without AA, respectively. The combination of S+AA generally provided the best performance of all the treatments. The combination of S+AA provided greater weight gain from 0 to 21, 0 to 42, 21 to 42 days and better FCR from 0 to 21, 0 to 42, and 21 to 42 days, lower NE mortality compared to both the S and the AACP treatments. The combination of S+AA also provided lower NE lesion scores compared to the AACP treatment.

The combination of CV+AA provided greater weight gain from days 0-21.0 to 42, 21 to 42 and better FCR from 0 to 21, 0 to 42, and 21 to 42 days compared to both the CV and the AACP treatments (Tables 3 and 4). The combination of CV+AA provided lower total mortality from days 0 to 42 and lower NE mortality compared to the CV and AACP treatments (Table 5).

Birds medicated with salinomycin with and without AA generally had the best performance and lower NE lesion scores and mortality comparable to or better than the NC. The addition of AA to the feeds of birds fed salinomycin tended to improve performance but did not further reduce NE lesion scores or mortality. Generally, the addition of AA to the feeds of birds treated with CV improved performance and reduced mortality compared to those treated with CV alone. Birds challenged with NE and treated with a conventional coccidiostat program or a coccidiosis vaccine program can benefit from the addition of AA to their feeds. Data in Tables 6, 7, and 8 allow for direct comparisons of the coccidiosis control programs to each other (with and without AA) and to the controls (challenged and unchallenged). During the 0 to 21 days period, birds fed S+AA had greater weight gains compared to the other treatments (Table 6). During the 0 to 21 days period, birds fed S had weight gains that were comparable to the NC but greater than the CP. During the 0 to 21 days period, birds vaccinated with CV had weight gains that were not different than the NC or CP birds. During the 0 to 42 and 21 to 42 days periods, birds treated with CV had greater weight gains compared to the CP birds.

During the 0 to 21 days period, birds fed S+AA had FCR that were better than the NC and CP birds (Table 7). During the 0 to 21 days period, birds medicated with S, CV, and CV+AA had FCR that were better than the CP birds. During the 0 to 42 and 21 to 42 days periods, birds treated with S, S+AA, CV, and CV+AA had FCR that were better than the NC and CP birds (Table 7). During the 0 to 42 days period, the addition of AA to the diets of birds treated with S and CV improved FCR compared to S and CV alone, respectively. During the 21 to 42 days periods the addition of AA to the diets of birds vaccinated with CV improved FCR compared to CV alone.

NE lesion scores of S and CV birds (with and without AA) were comparable to the NC but lower than the CP birds (Table 8). The treatments did not affect mortality during the 0 to 21 days period (Table 8). Mortality (total and NE) of the S, S+AA, and CV+AA birds were comparable to the NC but lower than the CP birds (Table 6). Mortality (total and NE) of CV birds was lower than the CP birds but higher than the NC birds. Mortality (total and NE) of birds treated with CV+AA was lower than with CV alone.

Example 4

One-day-old healthy male broiler chicks (Cobb×Cobb) were obtained from a hatchery where they were sexed and received routine vaccination (HVTSB1). Only healthy-appearing chicks were used in the study. No birds were replaced during the course of the study. Upon arrival, chicks were raised in litter floor pens. There were 50 birds placed per pen. Pens were blocked by location in the house. Each treatment appeared once within each block. Thermostatically-controlled gas furnaces maintained uniform temperature. Water was available ad libitum throughout the trial.

All birds were weighed by pen on days 0, 21, and 42. Starter, grower, and finisher feed consumptions were measured from days 0 to 21, 21 to 35, and 35 to 42, respectively. The study was terminated on day 42. On Day 22, five birds from each pen were lesion scored for NE. The scoring was based on a 0 to 3 score, with 0 being normal and 3 being the most severe. The scoring was as follows: 0 for normal intestines, 1 for slight mucus covering and loss of tone, 2 for severe necrotizing enteritis, and 3 for extreme necrotizing enteritis with presence of blood in the lumen. Birds dying during the study were weighed and necropsied for the presence of NE. All birds from the study were disposed of at the research facility. Mortality was summarized as total and those resulting from NE.

A total of nine different regimens were tested. All groups were challenged orally with *Eimeria maxima* (5,000 oocysts per bird) on Day 14. All treatments except a non-challenged control (NC) were challenged with *C. perfringens* (broth culture of *C. perfringens* $10^8$ cfu/ml) on days 19, 20, and 21. Control feeds did not contain Serenade® MAX (QST), Alphamune® (AM), or Salinomycin (S). Control groups were not spray vaccinated using a Spraycox® machine with the label recommended dosage on day of hatch. The groups were designated as follows:

Group NC (unchallenged control): Group NC was fed an unmedicated commercial type chicken starter ration compounded with feedstuffs commonly used in the United States and was unchallenged by *C. perfringens*.

Group CP (challenged control): Group CP was fed an unmedicated commercial type chicken starter ration compounded with feedstuffs commonly used in the United States and was challenged by *C. perfringens* as described above.

Group AM, CP (Alphamune® fed; challenged): Group AM, CP was fed a commercial type chicken starter ration compounded with feedstuffs commonly used in the United States plus Alphamune® at a rate of 1 pound per ton. This group was challenged.

Group QST, CP (Serenade® MAX fed; challenged) was fed a commercial type chicken starter ration compounded with feedstuffs commonly used in the United States plus Serenade® MAX at a rate of 0.25 pound per ton. This group was challenged as described above.

Group AQST, CP (Alphamune® and Serenade® MAX fed, challenged) was fed a commercial type chicken starter ration compounded with feedstuffs commonly used in the United States plus Alphamune® at a rate of 1 pound per ton and Serenade® MAX at a rate Of 0.25 pound per ton, and was challenged as described above.

Group S, CP (salinomycin treated; challenged) was fed a commercial type chicken starter ration compounded with feedstuffs commonly used in the United States plus salinomycin (66 ppm). This group was challenged as described above.

Group S, AQST, CP (salinomycin treated, Alphamune® and Serenade® MAX fed; challenged) was fed a commercial type chicken starter ration compounded with feedstuffs commonly used in the United States plus Alphamune® and Serenade® MAX at a rate of 1.25 pounds per ton and treated with salinomycin (66 ppm). This group was challenged as described above.

Group CV, CP (Coccivac®-B treated; challenged) was spray vaccinated using a Spraycox® machine with the label recommended dosage on day of hatch and fed was fed a commercial type chicken starter ration compounded with feedstuffs commonly used in the United States. This group was challenged as described above.

Group CV, AQST, CP (Coccivac®-B treated, Alphamune® and Serenade® MAX fed; challenged) was spray vaccinated using a Spraycox® machine with the label recommended dosage on day of hatch and fed was fed a commercial type chicken starter ration compounded with feedstuffs commonly used in the United States plus Alphamune® and Serenade® MAX at a rate of 1.25 pounds per ton. This group was challenged as described above.

Statistics were carried out using SAS® (SAS Institute, Inc., Cary, N.C., USA, 2002) in the analyses of the data. Additional analyses were performed comparing AA with the anticoccidial program with and without AA.

Calculations of pen data used in the statistical analyses were performed using SAS. Average bird weight gains were calculated for the 0 to 21, 0 to 42, and 21 to 42-days periods. For the NE lesion scores, the pen average of the five birds selected for NE lesion scoring on Day 22 were calculated. The feed conversion ratio (FCR) was calculated on a pen basis for the 0 to 21, 0 to 42, and 21 to 42 days periods with adjustments made for dead and removed birds. The percentages of total mortality and those mortalities caused by NE were calculated. Any reference made to the performance of the chickens would be referring to effects on weight gain and/or FCR.

This study was conducted using a randomized complete block design.

There were 6 blocks. The pen of birds was the experimental unit. The model included block and treatment. Block was a random effect. Treatment was a fixed effect, so the model was mixed.

The summary variables include performance data and data related to the NE challenge for each pen. A mixed model analysis was performed on the data using the PROC MIXED procedure of SAS.

The results of the trials are shown in Tables 9-17. In the tables the following abbreviations are used:
AM=Alphamune®
QST=Serenade® MAX
AQST=Alphamune plus Serenade® MAX
S=salinomycin
CV=Coccivac®-B
CP=Challenged
NC=Not Challenged

TABLE 9

Effects of dietary Alphamune plus QST on weight gains of broiler chickens in a *Clostridium perfringens* challenge model in litter floor pens.

| Treatments[1] | Average weight (kg) Day 0 | Average Weight Gain (kg) | | |
|---|---|---|---|---|
| | | Days 0 to 21 | Days 0 to 42 | Days 21 to 42 |
| Control (NC) | .044 | .615 | 1.829 | 1.214 |
| Challenged Control (CP) | .044 | .514 | 1.753 | 1.238 |
| AM, CP | .045 | .579 | 1.840 | 1.261 |
| QST, CP | .044 | .595 | 1.825 | 1.230 |
| AQST, CP | .044 | .619 | 1.891 | 1.273 |
| S, CP | .044 | .592 | 1.856 | 1.264 |
| S, AQST, CP | .044 | .605 | 1.872 | 1.266 |
| CV, CP | .044 | .554 | 1.840 | 1.286 |
| CV, AQST, CP | .045 | .574 | 1.883 | 1.310 |

TABLE 10

Effects of dietary Alphamune plus QST on feed conversion and necrotic enteritis lesions of broiler chickens in a *Clostridium perfringens* challenge model in litter floor pens.

| Treatments | Feed Conversion Ratio (feed to gain ratio) | | | Necrotic Enteritis Lesion Score |
|---|---|---|---|---|
| | Days 0 to 21 | Days 0 to 42 | Days 21 to 42 | |
| Control (NC) | 1.573 | 1.996 | 2.261 | 0.13 |
| Challenged Control (CP) | 1.818 | 2.025 | 2.156 | 0.90 |
| AM, CP | 1.624 | 1.983 | 2.196 | 0.20 |
| QST, CP | 1.612 | 1.991 | 2.234 | 0.30 |
| AQST, CP | 1.566 | 1.953 | 2.192 | 0.13 |
| S, CP | 1.550 | 1.914 | 2.126 | 0.10 |
| S, AQST, CP | 1.551 | 1.903 | 2.111 | 0.17 |
| CV, CP | 1.710 | 1.957 | 2.094 | 0.20 |
| CV, AQST, CP | 1.611 | 1.918 | 2.094 | 0.07 |

TABLE 11

Effects of dietary Alphamune plus QST on mortality of broiler chickens in a *Clostridium perfringens* challenge model in litter floor pens.

| Treatments | Mortality (%) | | |
|---|---|---|---|
| | All Causes | | Necrotic Enteritis |
| | Days 0 to 21 | Days 0 to 42 | Days 0 to 42 |
| Control (NC) | 1.33 | 3.33 | 0.33 |
| Challenged Control (CP) | 6.67 | 18.33 | 15.33 |
| AM, CP | 2.00 | 6.00 | 3.00 |
| QST, CP | 1.67 | 6.67 | 5.33 |
| AQST, CP | 0.67 | 5.33 | 3.00 |
| S, CP | 1.67 | 4.67 | 1.33 |
| S, AQST, CP | 1.33 | 3.33 | 1.00 |

TABLE 11-continued

Effects of dietary Alphamune plus QST on mortality of broiler chickens in a *Clostridium perfringens* challenge model in litter floor pens.

| | Mortality (%) | | |
| --- | --- | --- | --- |
| | All Causes | | Necrotic Enteritis |
| Treatments | Days 0 to 21 | Days 0 to 42 | Days 0 to 42 |
| CV, CP | 4.67 | 8.6 | 5.33 |
| CV, AQST, CP | 2.67 | 7.33 | 3.00 |

TABLE 12

Effects of dietary Alphamune plus QST on weight gains of broiler chickens in a *Clostridium perfringens* challenge model in litter floor pens.

| | | Average Weight Gain (kg) | | |
| --- | --- | --- | --- | --- |
| Treatments | Average weight (kg) Day 0 | Days 0 to 21 | Days 0 to 42 | Days 21 to 42 |
| Control (NC) | .044 | .615 | 1.829 | 1.214 |
| Challenged Control (CP) | .044 | .514 | 1.753 | 1.238 |
| AM, CP | .045 | .579 | 1.840 | 1.261 |
| QST, CP | .044 | .595 | 1.825 | 1.230 |
| AQST, CP | .044 | .619 | 1.891 | 1.273 |

TABLE 13

Effects of dietary Alphamune plus QST on feed conversion and necrotic enteritis lesions of broiler chickens in a *Clostridium perfringens* challenge model in litter floor pens.

| | Feed Conversion Ratio (feed to gain ratio) | | | Necrotic Enteritis Lesion Score |
| --- | --- | --- | --- | --- |
| Treatments | Days 0 to 21 | Days 0 to 42 | Days 21 to 42 | |
| Control (NC) | 1.573 | 1.996 | 2.261 | 0.13 |
| Challenged Control (CP) | 1.818 | 2.025 | 2.156 | 0.90 |
| AM, CP | 1.624 | 1.983 | 2.196 | 0.20 |
| QST, CP | 1.612 | 1.991 | 2.234 | 0.30 |
| AQST, CP | 1.566 | 1.953 | 2.192 | 0.13 |

TABLE 14

Effects of dietary Alphamune plus QST on mortality of broiler chickens in a *Clostridium perfringens* challenge model in litter floor pens.

| | Mortality (%) | | |
| --- | --- | --- | --- |
| | All Causes | | Necrotic Enteritis |
| Treatments | Days 0 to 21 | Days 0 to 42 | Days 0 to 42 |
| Control (NC) | 1.33 | 3.33 | 0.33 |
| Challenged Control (CP) | 6.67 | 18.33 | 15.33 |
| AM, CP | 2.00 | 6.00 | 3.00 |
| QST, CP | 1.67 | 6.67 | 5.33 |
| AQST, CP | 0.67 | 5.33 | 3.00 |

TABLE 15

Effects of dietary Alphamune plus QST on weight gains of broiler chickens in a *Clostridium perfringens* challenge model in litter floor pens.

| | | Average Weight Gain (kg) | | |
| --- | --- | --- | --- | --- |
| Treatments | Average weight (kg) Day 0 | Days 0 to 21 | Days 0 to 42 | Days 21 to 42 |
| Control (NC) | .044 | .615 | 1.829 | 1.214 |
| Challenged Control (CP) | .044 | .514 | 1.753 | 1.238 |
| AQST, CP | .044 | .619 | 1.891 | 1.273 |
| S, CP | .044 | .592 | 1.856 | 1.264 |
| S, AQST, CP | .044 | .605 | 1.872 | 1.266 |
| CV, CP | .044 | .554 | 1.840 | 1.286 |
| CV, AQST, CP | .045 | .574 | 1.883 | 1.310 |

TABLE 16

Effects of dietary Alphamune plus QST on feed conversion and necrotic enteritis lesions of broiler chickens in a *Clostridium perfringens* challenge model in litter floor pens.

| | Feed Conversion Ratio (feed to gain ratio) | | | Necrotic Enteritis Lesion Score |
| --- | --- | --- | --- | --- |
| Treatments | Days 0 to 21 | Days 0 to 42 | Days 21 to 42 | |
| Control (NC) | 1.573 | 1.996 | 2.261 | 0.13 |
| Challenged Control (CP) | 1.818 | 2.025 | 2.156 | 0.90 |
| AQST, CP | 1.566 | 1.953 | 2.192 | 0.13 |
| S, CP | 1.550 | 1.914 | 2.126 | 0.10 |
| S, AQST, CP | 1.551 | 1.903 | 2.111 | 0.17 |
| CV, CP | 1.710 | 1.957 | 2.094 | 0.20 |
| CV, AQST, CP | 1.611 | 1.918 | 2.094 | 0.07 |

TABLE 17

Effects of dietary Alphamune plus QST on mortality of broiler chickens in a *Clostridium perfringens* challenge model in litter floor pens.

| | Mortality (%) | | |
| --- | --- | --- | --- |
| | All Causes | | Necrotic Enteritis |
| Treatments | Days 0 to 21 | Days 0 to 42 | Days 0 to 42 |
| Control (NC) | 1.33 | 3.33 | 0.33 |
| Challenged Control (CP) | 6.67 | 18.33 | 15.33 |
| AQST, CP | 0.67 | 5.33 | 3.00 |
| S, CP | 1.67 | 4.67 | 1.33 |
| S, AQST, CP | 1.33 | 3.33 | 1.00 |
| CV, CP | 4.67 | 8.67 | 5.33 |
| CV, AQST, CP | 2.67 | 7.33 | 3.00 |

The addition of AM, QST, and AQST to the feeds of broiler chickens improved performance compared to the CC. Birds medicated with salinomycin with and without AQST generally had the best performance and lower NE lesions and mortality comparable to or better than the NC. Generally, the addition of AQST to the feeds of birds treated with Coccivac improved performance and reduced mortality compared to those treated with Coccivac alone.

The invention claimed is:

1. A composition for the treatment of a disease in an animal comprising: yeast extract from *Saccharomyces cerevisiae*, *Bacillus licheniformis* spores, and optionally a carrier, wherein about 50 wt.% to about 90 wt.% of the cell wall fraction from *Saccharomyces cerevisiae*, about 5 wt.% to about 50 wt.% of the *Bacillus licheniformis* spores, comprising, about $4.5 \times 10^9$ to about $2.5 \times 10^{10}$ spores per gram, and about 0 wt.% to about 45 wt.% of the carrier.

2. The composition of claim 1, comprising
   (a) 50 wt.% of the cell wall fraction from *Saccharomyces cerevisiae*,
   (b) 10 wt.% of the *Bacillus licheniformis* spores, comprising about $5 \times 10^9$) to about $1.25 \times 10^{10}$ spores per gram, and
   (c) 40 wt.% of the carrier.

3. The composition of claim 1 wherein the carrier comprises calcium carbonate calcium sulfate, lactose, or a combination thereof.

4. An animal feed composition comprising the composition for the treatment of a disease in an animal of any one of claim 1, 2, or 3, and an animal foodstuff, wherein the composition for the treatment of a disease in an animal is in an amount of about 0.5 pounds to about 10 pounds per ton of the animal foodstuff.

5. The animal feed composition of claim 4, wherein the composition for the treat a disease in an animal is in an amount of about 1 pound to about 5 pounds per ton of the animal foodstuff.

6. The animal feed composition of claim 5, wherein the composition for the treatment of a disease in an animal is in an amount of about 2 pounds per ton of the animal foodstuff.

7. The animal feed composition of claim 6, wherein animal foodstuff is a poultry foodstuff or a swine foodstuff.

* * * * *

UNITED STATES PATENT AND TRADEMARK OFFICE
CERTIFICATE OF CORRECTION

PATENT NO. : 8,227,235 B2
APPLICATION NO. : 12/586359
DATED : July 24, 2012
INVENTOR(S) : Skinner et al.

Page 1 of 1

It is certified that error appears in the above-identified patent and that said Letters Patent is hereby corrected as shown below:

Column 16, lines 64 and 67, "lichenformis" should read "licheniformis".

Column 17, line 7, "5×109)" should read "$5 \times 10^9$".

Column 18, line 5, "treat" should read "treatment of".

Signed and Sealed this
Eleventh Day of September, 2012

David J. Kappos
*Director of the United States Patent and Trademark Office*